(12) United States Patent
Kim

(10) Patent No.: US 10,702,322 B2
(45) Date of Patent: Jul. 7, 2020

(54) MEDICAL INSERTION APPARATUS

(71) Applicant: Kyungpook National University Industry-Academic Cooperation Foundation, Daegu (KR)

(72) Inventor: Kyoung Tae Kim, Daegu-si (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 712 days.

(21) Appl. No.: 14/467,837

(22) Filed: Aug. 25, 2014

(65) Prior Publication Data
US 2015/0057711 A1 Feb. 26, 2015

(30) Foreign Application Priority Data

Mar. 24, 2014 (KR) .................. 10 2014 0034202
Mar. 24, 2014 (KR) .................. 10 2014 0034203

(51) Int. Cl.
| | | |
|---|---|---|
| *A61B 17/86* | (2006.01) | |
| *A61N 1/05* | (2006.01) | |
| *A61B 5/00* | (2006.01) | |
| *A61B 17/70* | (2006.01) | |
| *A61B 5/0492* | (2006.01) | |
| *A61C 8/00* | (2006.01) | |
| *A61N 1/36* | (2006.01) | |
| *A61C 19/04* | (2006.01) | |
| *A61B 17/00* | (2006.01) | |

(52) U.S. Cl.
CPC .......... *A61B 17/866* (2013.01); *A61B 5/0492* (2013.01); *A61B 5/4836* (2013.01); *A61B 5/4893* (2013.01); *A61B 17/70* (2013.01); *A61B 17/7032* (2013.01); *A61B 17/864* (2013.01); *A61B 17/8625* (2013.01); *A61C 8/0039* (2013.01); *A61N 1/05* (2013.01); *A61N 1/0551* (2013.01); *A61B 2017/00022* (2013.01); *A61B 2017/0073* (2013.01); *A61C 8/0022* (2013.01); *A61C 8/0089* (2013.01); *A61C 19/04* (2013.01); *A61N 1/0558* (2013.01); *A61N 1/36014* (2013.01)

(58) Field of Classification Search
CPC . A61B 17/866; A61B 17/864; A61B 17/8685; A61B 17/8625; A61B 17/7032; A61B 2017/00022; A61B 2017/00026
See application file for complete search history.

(56) References Cited

U.S. PATENT DOCUMENTS

| | | | |
|---|---|---|---|
| 2004/0243207 A1 | 12/2004 | Olson et al. | |
| 2008/0125637 A1* | 5/2008 | Geist | A61B 5/0492 600/372 |
| 2009/0125072 A1* | 5/2009 | Neubardt | A61B 17/8625 606/305 |

(Continued)

*Primary Examiner* — Amy R Sipp
(74) *Attorney, Agent, or Firm* — Boyle Fredrickson S.C.

(57) ABSTRACT

Provided are a medical insertion apparatus includes a screw body to be inserted into a body, and an electrode provided in the screw body and including an externally exposed portion, wherein a through-hole may be provided in the screw body or the electrode, and a medical insertion apparatus includes a screw body to be inserted into a body, and an electrode provided in the screw body and exposed to an outside of the screw body, wherein the screw body and the electrode may be provided in a connectable or separable structure.

4 Claims, 12 Drawing Sheets

(56) References Cited

U.S. PATENT DOCUMENTS

2010/0106198 A1* 4/2010 Adcox ............... A61B 17/8625
 606/301
2011/0144702 A1 6/2011 Leroux et al.
2016/0038205 A1* 2/2016 Smith ................. A61B 17/866
 606/304

* cited by examiner

MEDICAL INSERTION APPARATUS

CROSS-REFERENCE TO RELATED APPLICATIONS

This application claims the benefit of Korean Patent Application Nos. 10-2013-0101078, filed on Aug. 26, 2013, 10-2014-0028345, filed on Mar. 11, 2014, 10-2014-0028921, filed on Mar. 12, 2014, 10-2014-0034206 filed on Mar. 24, 2014, 10-2014-0034210, filed on Mar. 24, 2014, 10-2014-0034202, filed on Mar. 24, 2014, and 10-2014-0034203, filed on Mar. 24, 2014, in the Korean Intellectual Property Office, the disclosures of which are incorporated herein by reference.

BACKGROUND

1. Field of the Invention

Embodiments of the present invention relate to a medical insertion apparatus, and more particularly, to a medical insertion apparatus that may be safely inserted into a body and facilitate a connection or separation between a screw body and an electrode.

2. Description of the Related Art

A medical insertion apparatus may include, for example, a pedicle screw, a spinal screw, a bone screw, and a dental implant.

In general, a patient with a spinal fracture or a partial spinal injury may be unable to perform activities. Although the patient has experienced a minor injury and thus may perform activities, recovery may progress slowly even with treatment, because an injured or fractured part of a spine may be pressed or touched by another adjacent part.

Thus, such a patient may require surgery to support an adjacent spinal part using an artificial device so that the fractured or injured part of the spine may not be pressed or compressed.

The artificial device used to support the spine may include a pedicle screw to be inserted on upper and lower sides of the injured part of the spine to act as a fixture, and a rod to be connected through the pedicle screw to act as a support.

In general, a pedicle screw used for such an insertion may include a monoaxial screw and a polyaxial screw. The monoaxial screw includes a head and a screw provided to be immobile to form an invariant angle, and the poly screw includes a head and a screw provided to form a variable angle.

The dental implant refers to a prosthesis to be implanted into an oral tissue such as, for example, an osseous tissue, and may be configured to be substituted for a lost tooth root.

The dental implant may recover an original dental function by inserting an artificial tooth root into an alveolar bone, performing osseous integration, and connecting an artificial tooth to the artificial tooth root. The artificial tooth root may be made of a biocompatible material such as titanium.

Recently, with an increase in spinal or dental treatment or surgery, research is being actively conducted on an apparatus to be inserted into a body.

For example, Korean Patent Application No. 2012-0074355, filed on Jul. 9, 2012, discloses a pedicle screw that includes a head portion and a screw rod in which a through-hole portion having a polygonal cross-section is provided.

SUMMARY

An aspect of the present invention provides a medical insertion apparatus that may increase an area of contact with nerves, thereby increasing a nerve detection efficiency and preventing neurological damage.

An aspect of the present invention provides a medical insertion apparatus that may increase a surgical stability and reduce a radiation exposure time during a surgery.

An aspect of the present invention provides a medical insertion apparatus that may be efficiently inserted into a body by means of a guide element configured to guide an insertion of a screw body into a body during a surgery.

An aspect of the present invention provides a medical insertion apparatus that may include a screw body provided in a form of a tapping screw, thereby detecting nerves while forming a hole through which the screw body is to be inserted.

An aspect of the present invention provides a medical insertion apparatus that may facilitate a connection or a separation between a screw body and an electrode.

An aspect of the present invention provides a medical insertion apparatus that may include a screw body and an electrode provided using materials having similar melting points.

An aspect of the present invention provides a medical insertion apparatus that may be processed in a form of an assembly, whereby a defect rate may decrease, processing may be easy, and a unit cost of production may decrease.

An aspect of the present invention provides a medical insertion apparatus that may easily maintain a screw body or an electrode.

According to an aspect of the present invention, there is provided a medical insertion apparatus including a screw body to be inserted into a body, and an electrode provided in the screw body, and including an externally exposed portion. A through-hole may be provided in the screw body or the electrode.

The through-hole may extend in a longitudinal direction of the screw body from one end of the screw body to a terminal portion of the screw body.

When the electrode is disposed in a central portion of the screw body, the through-hole may be provided in a central portion of the electrode.

A guide element may be disposed in the through-hole to guide an insertion of the screw body into the body.

The externally exposed portion of the electrode may be provided at a terminal portion of the screw body.

The externally exposed portion of the electrode may be provided at a position spaced apart from a terminal portion of the screw body on an outer circumference of the screw body.

The externally exposed portion of the electrode may be provided in a form of a ring shape along the outer circumference of the screw body.

The electrode may extend to be perpendicular or to incline from the central portion of the screw body toward the outer circumference of the screw body.

The screw body may be provided in a form of a tapping screw.

According to another aspect of the present invention, there is provided a medical insertion apparatus including a screw body to be inserted into a body, and an electrode provided in the screw body and exposed to an outside of the screw body. The screw body and the electrode may be provided in a connectable or separable structure.

The electrode may be inserted through a terminal portion of the screw body and connected to the screw body through screw fastening.

The electrode may include a first portion to extend in a longitudinal direction of the screw body, and a second portion connected to the first portion and externally exposed at the terminal portion of the screw body. A thread may be provided on a portion of the first portion.

A through-hole through which the first portion is to be inserted may be provided in the screw body, and a thread to engage with the thread of the first portion may be provided in the through-hole.

The thread of the first portion and the thread of the through-hole may be provided at positions adjacent to the terminal portion of the screw body.

When the first portion is connected to the through-hole through screw fastening, one end of the first portion and one end of the screw body may be disposed at identical heights.

The electrode may include a third portion to extend in a longitudinal direction of the screw body toward one side of the screw body, and a fourth portion to be connected to an end portion of the third portion and to externally protrude on the one side of the screw body.

To connect the third portion and the fourth portion, a recessed element and a protruding element may be provided symmetrically at the third portion and the fourth portion, respectively.

The electrode may be inserted through one end of the screw body and connected to the screw body through screw fastening.

To restrict a separation between the screw body and the electrode after the screw body and the electrode are connected to each other, a guide recess and a guide protrusion may be provided symmetrically at one end of the screw body and one end of the electrode, respectively.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
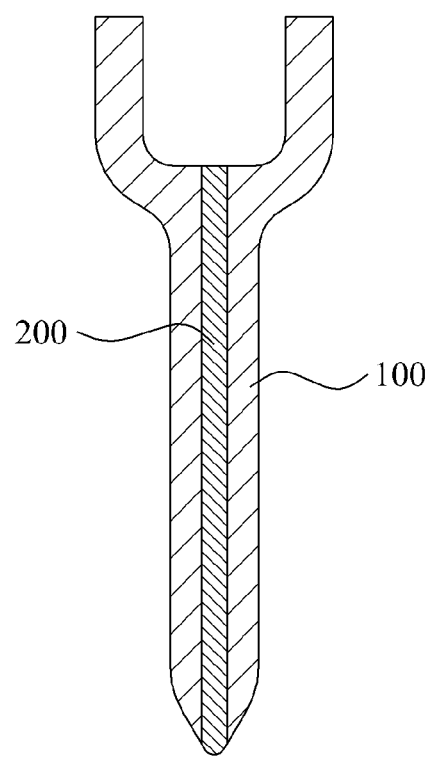
FIG. 1 is a view illustrating a medical insertion apparatus according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 2A:
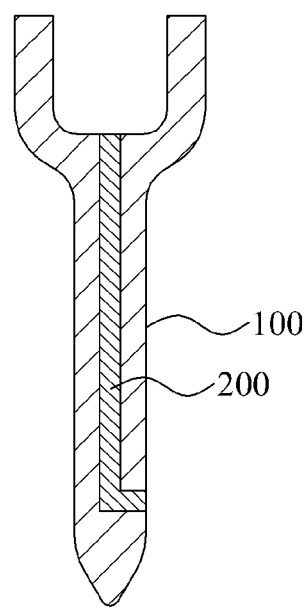
FIGS. 2A and 2B are views illustrating an electrode extending to be perpendicular or to incline with respect to a screw body in a medical insertion apparatus according to an embodiment of the present invention.
Figure 2B:
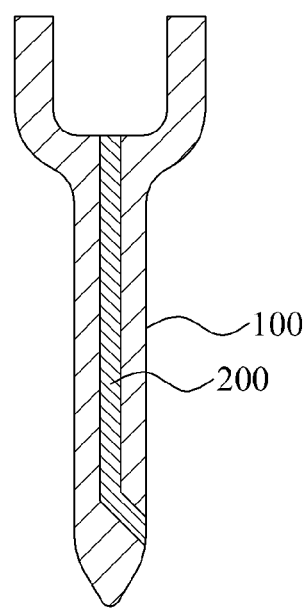
Figure 3A:
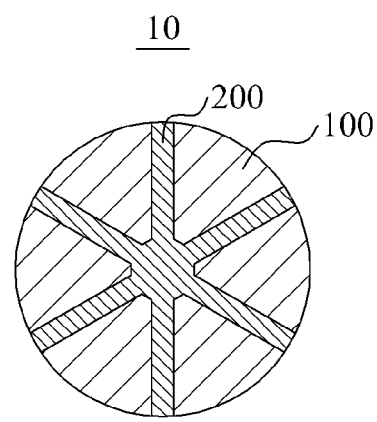
FIGS. 3A and 3B are views illustrating an electrode exposed at a plurality of positions in a medical insertion apparatus according to an embodiment of the present invention.
Figure 3B:
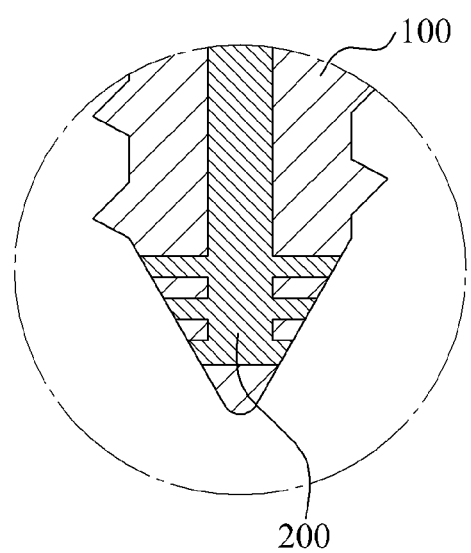
Figure 4:
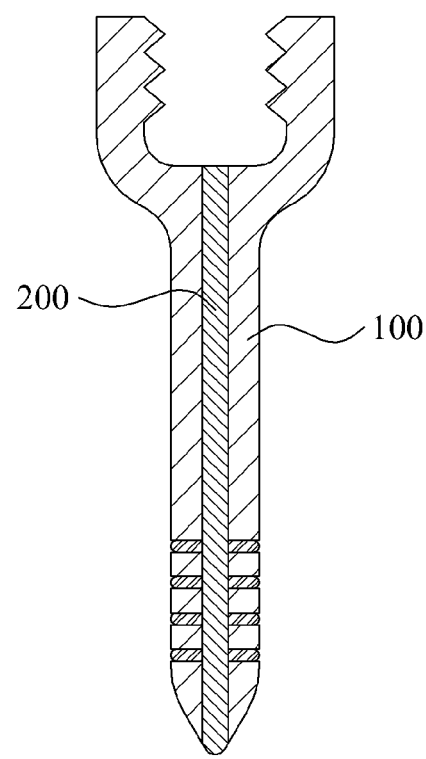
FIG. 4 is a view illustrating an electrode having an externally exposed portion provided in a form of a ring shape in a medical insertion apparatus according to an embodiment of the present invention.
Figure 5:
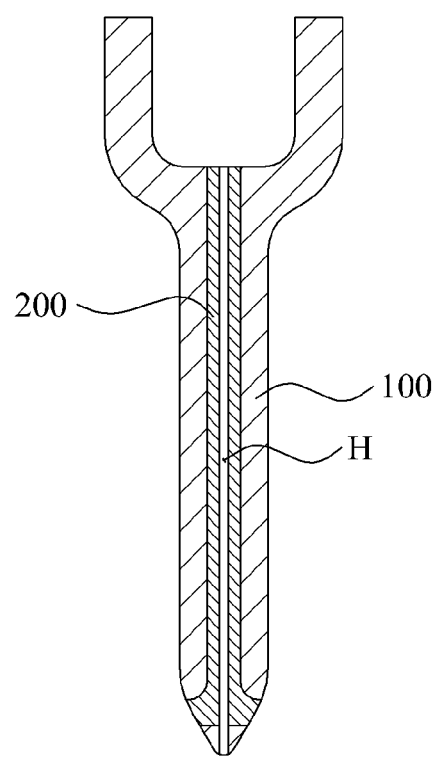
FIG. 5 is a view illustrating a through-hole provided in a screw body or an electrode in a medical insertion apparatus according to an embodiment of the present invention.
Figure 6:
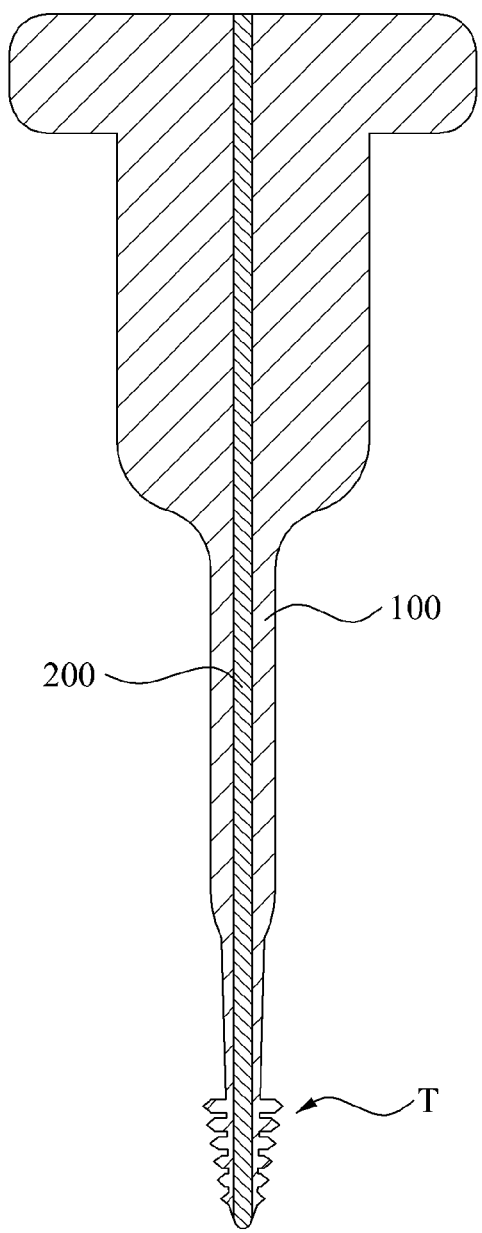
FIG. 6 is a view illustrating a screw body provided in a form of a tapping screw in a medical insertion apparatus according to an embodiment of the present invention.

FIG. 1 is a view illustrating a medical insertion apparatus 10 according to an embodiment of the present invention. FIGS. 2A and 2B are views illustrating an electrode 200 extending to be perpendicular or to incline with respect to a screw body 100 in the medical insertion apparatus 10 according to an embodiment of the present invention. FIGS. 3A and 3B are views illustrating the electrode 200 exposed at a plurality of positions in the medical insertion apparatus 10 according to an embodiment of the present invention. FIG. 4 is a view illustrating the electrode 200 having an externally exposed portion provided in a form of a ring shape in the medical insertion apparatus 10 according to an embodiment of the present invention. FIG. 5 is a view illustrating a through-hole provided in the screw body 100 or the electrode 200 in the medical insertion apparatus 10 according to an embodiment of the present invention. FIG. 6 is a view illustrating the screw body 100 provided in a form of a tapping screw in the medical insertion apparatus 10 according to an embodiment of the present invention.

Referring to FIG. 1, the medical insertion apparatus 10 includes the screw body 100 and the electrode 200.

The screw body 100 may be inserted into a body. A thread may be provided on an outer side of the screw body 100.

The screw body 100 may be inserted into a spine, a tooth, or a muscle. For example, the screw body 100 may be configured in a synostosis screw to be inserted into an osseous tissue adjacent to a nerve, in particular, a pedicle screw to be inserted into a spine.

Thus, the screw body 100 may be manufactured using titanium. Titanium is excellent in terms of biocompatibility and strength, and thus may be used as a material for a variety of implants.

The electrode 200 is provided in a central portion of the screw body 100.

The electrode 200 extends in a longitudinal direction of the screw body 100 from one end of the screw body 100 to a terminal portion of the screw body 100.

A hole (not shown) in which the electrode 200 is to be disposed may be provided in the central portion of the screw body 100 to penetrate through the screw body 100 from the one end of the screw body 100 to the terminal portion of the screw body 100.

The electrode 200 may be formed using a method of filling the hole with a melted electrode material and hardening the electrode material by cooling the electrode material at room temperature.

For example, several protrusions or recesses may be formed on an inner circumferential surface of the hole, the hole may be filled with the melted electrode material, and the electrode material may be hardened. In this example, the electrode 200 may be more strongly fixed in the hole. Thus, the electrode 20 may be stably disposed in the screw body 100.

A material of the electrode 200 may include platinum, gold, silver, tungsten, and any material verified to be biocompatible and have an excellent electric conductivity, and thus be suitable for detecting a minute signal.

As illustrated in FIG. 1, the electrode 200 is externally exposed at the terminal portion of the screw body 100.

Since the electrode 200 is externally exposed only at the terminal portion of the screw body 100, the medical insertion apparatus 10 may be manufactured through relatively simple molding.

In addition, the electrode 200 may be exposed at a portion of the screw body 100 to be in contact with a nerve first. Thus, a nerve may be detected relatively early when the medical insertion apparatus 10 is inserted into a body.

As shown in FIGS. 2A and 2B, the electrode 200 may be exposed on an outer circumference of the screw body 100 at a position spaced apart from the terminal portion of the screw body 100.

Referring to FIG. 2A, the electrode 200 extends to be perpendicular from the central portion of the screw body 100 toward the outer circumference of the screw body 100.

The electrode 200 extending in the longitudinal direction of the screw body 100 extends in a direction perpendicular to the longitudinal direction of the screw body 100 and is externally exposed at a position spaced apart from the terminal portion of the screw body 100 on the outer circumference of the screw body 100.

In this example, a distance between the electrode 200 disposed in the central portion of the screw body 100 and the terminal portion of the screw body 100 may be equal to a distance between the externally exposed portion of the electrode 200 and the terminal portion of the screw body 100.

Referring to FIG. 2B, the electrode 200 extends to incline from the central portion of the screw body 100 toward the outer circumference of the screw body 100.

The electrode 200 extending in the longitudinal direction of the screw body 100 extends in a direction inclined with respect to the longitudinal direction of the screw body 100 and is externally exposed at a position spaced apart from the terminal portion of the screw body 100 on the outer circumference of the screw body 100.

In this example, a distance between the electrode 200 disposed in the central portion of the crew body 100 and the terminal portion of the screw body 100 may be greater than or less than a distance between the externally exposed portion of the electrode 200 and the terminal portion of the screw body 100.

As described above, the electrode 200 is externally exposed at a position spaced apart from the terminal portion of the screw body 100. Thus, a nerve monitoring range may be broadened.

As illustrated in FIGS. 3A and 3B, the electrode 200 may be exposed at a plurality of positions.

Referring to FIG. 3A, the electrode 200 is externally exposed in a radial shape on the outer circumference of the screw body 100.

The electrode 200 extending in the longitudinal direction of the screw body 100 extends to be perpendicular or to incline with respect to the longitudinal direction of the screw body 100 and is externally exposed at a position spaced apart from the terminal portion of the screw body 100 on the outer circumference of the screw body 100.

In this example, the electrode 200 extends in a radial direction from the central portion of the screw body 100 toward the outer circumference of the screw body 100.

Through the electrode 200 configured as described above, the medical insertion apparatus 10 may monitor nerves in many ways with respect to the screw body 100.

Referring to FIG. 3B, the electrode 200 is externally exposed in a multi-stage shape on the outer circumference of the screw body 100.

The electrode 200 extending in the longitudinal direction of the screw body 100 extends to be perpendicular or to incline with respect to the longitudinal direction of the screw body 100 and is externally exposed at a position spaced apart from the terminal portion of the screw body 100 on the outer circumference of the screw body 100.

In this example, the electrode 200 extends in the multi-stage shape from the central portion of the screw body 100 toward the outer circumference of the screw body 100.

FIG. 3B illustrates the electrode 100 externally exposed in the multi-stage shape only at an end portion of the screw body 100. However, a position at which the electrode 100 is externally exposed is not limited thereto. The electrode 100 may be externally exposed in the multi-stage shape at various positions on the outer circumference of the screw body 100.

Through the electrode 200 configured as described above, the medical insertion apparatus 10 may efficiently monitor nerves positioned at different heights with respect to the screw body 100.

As illustrated in FIG. 4, the electrode 200 may be externally exposed in a form of a ring shape.

Referring to FIG. 4, the electrode 200 is externally exposed in the form of a ring shape along the outer circumference of the screw body 100 and at the terminal portion of the screw body 100.

The externally exposed portion of the electrode 200 provided in the form of the ring shape is disposed at a position spaced apart from the terminal portion of the screw body on the outer circumference of the screw body 100.

The externally exposed portion of the electrode 200 provided in the form of the ring shape may be integrated with the screw body 100, or formed separately from the screw body 100 to be detachable.

A plurality of ring shapes may be provided. The plurality of ring shapes may be disposed to be spaced from each other in the longitudinal direction of the screw body 100.

The ring shapes may be provided at a portion of the screw body 100. For example, the ring shapes may be provided over a half of the screw body 100.

The ring shapes may be provided over the entire screw body 100. Thus, the electrode 200 may be externally exposed over the entire screw body 100.

In this example, the electrode 200 extending in the longitudinal direction of the screw body 100 extends in a direction perpendicular or inclined with respect to the longitudinal direction of the screw body 100, and is connected to the externally exposed portion of the electrode 200 provided in the form of the ring shape.

As described above, when the electrode 100 is externally exposed at more positions, an area of contact with nerves may increase and nerves may be detected more efficiently. Thus, when the medical insertion apparatus 10 is inserted into a body, neurological damage may be prevented.

Referring to FIG. 5, a through-hole H is provided in a central portion of the screw body 100 or the electrode 200.

The through-hole H is provided in the longitudinal direction of the screw body 100 or the electrode 200 from one end of the screw body 100 or the electrode 200 toward the terminal portion of the screw body 100. For example, the through-hole H may be provided in a form of a tunnel or a small hole having a diameter of about 1 millimeter (mm) When the electrode 200 extends in the longitudinal direction of the screw body 100 from the one end of the screw body 100 and is externally exposed at a position spaced apart from the terminal portion of the screw body 100 on the outer circumference of the screw body 100, the through-hole H may be provided to extend from the one end of the screw body 100 or the electrode 200 in the longitudinal direction of the screw body 100 or the electrode 200. In this example, the through-hole H may be provided straightly to penetrate through the electrode 200 and the terminal portion of the screw body 100.

When the electrode 200 extends in the longitudinal direction of the screw body 100 from the one end of the screw body 100 and is externally exposed at the terminal portion of the screw body 100, the through-hole H may be provided straightly to extend in the longitudinal direction of the screw body 100 or the electrode 200 from the one end of the screw body 100 or the electrode 200 and penetrate through the terminal portion of the screw body 100 or the electrode 200.

Thus, the through-hole H may be referred to as being provided in the central portion of the electrode 200, and also be referred to as being provided in the central portion of the screw body 100.

FIG. 5 illustrates the electrode 200 being externally exposed at a position spaced apart from the terminal portion of the screw body 100 on the outer circumference of the screw body 100. However, a position at which the electrode 200 is externally exposed is not limited thereto. The electrode 200 may be externally exposed at various positions of the screw body 100 as described above.

A guide element (not shown) may be disposed in the through-hole H provided in the electrode 200.

The guide element may guide an insertion of the screw body 100 into a body, and may be provided using, for example, a wire, a cable, and a string.

In detail, during a minimally invasive surgery, a wire may be inserted into a spine to pass through the through-hole H of the screw body 100 or the electrode 200. The screw body 100 may be inserted into the body along a path of the wire.

Thus, the medical insertion apparatus 10 may be more easily inserted into a body, and a surgical stability may increase.

Referring to FIG. 6, the screw body 100 is provided in a form of a tapping screw T.

The tapping screw T may be used to perform boring before the screw body 100 is inserted into a body.

The screw body 100 may be inserted into a body more safely through a hole provided by the tapping screw T.

The electrode 200 may be provided to be externally exposed on a side on which the tapping screw T is provided. Thus, a contact between the screw body 100 and a nerve may be detected during the boring.

FIG. 6 illustrates the electrode 200 being exposed at the terminal portion of the screw body 100. However, it is obvious that the electrode 200 may be exposed at a position spaced apart from the terminal portion of the screw body 100 on the outer circumference of the screw body 100.

As described above, the medical insertion apparatus 10 may increase an area of contact with nerves, thereby efficiently detecting a nerve, preventing neurological damage, increasing a surgical stability, and reducing a radiation exposure time during a surgery. In addition, the medical insertion apparatus 10 may be efficiently inserted into a body by means of a guide element configured to guide an insertion of a screw body into a body during a surgery. The medical insertion apparatus 10 may include a screw body provided in a form of a tapping screw to detect a nerve while forming a hole through which the screw body is to be inserted.

Figure 7:
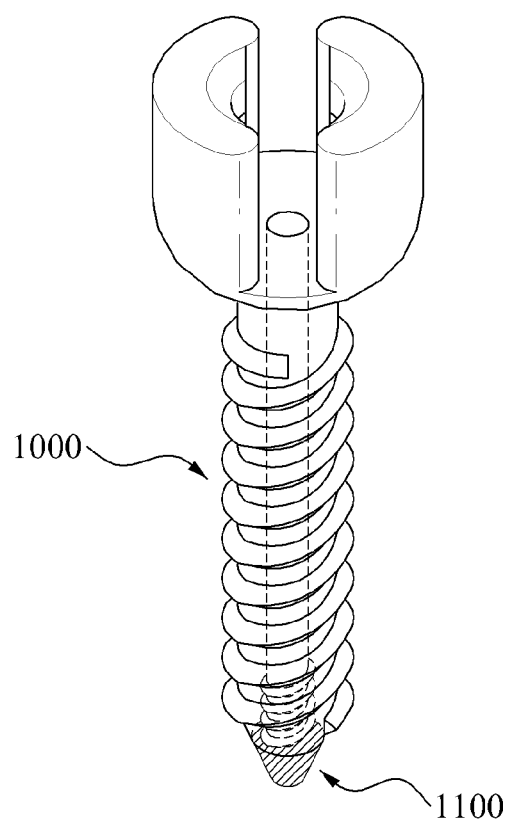
FIG. 7 is a view illustrating a medical insertion apparatus according to another embodiment of the present invention.
Figure 8:
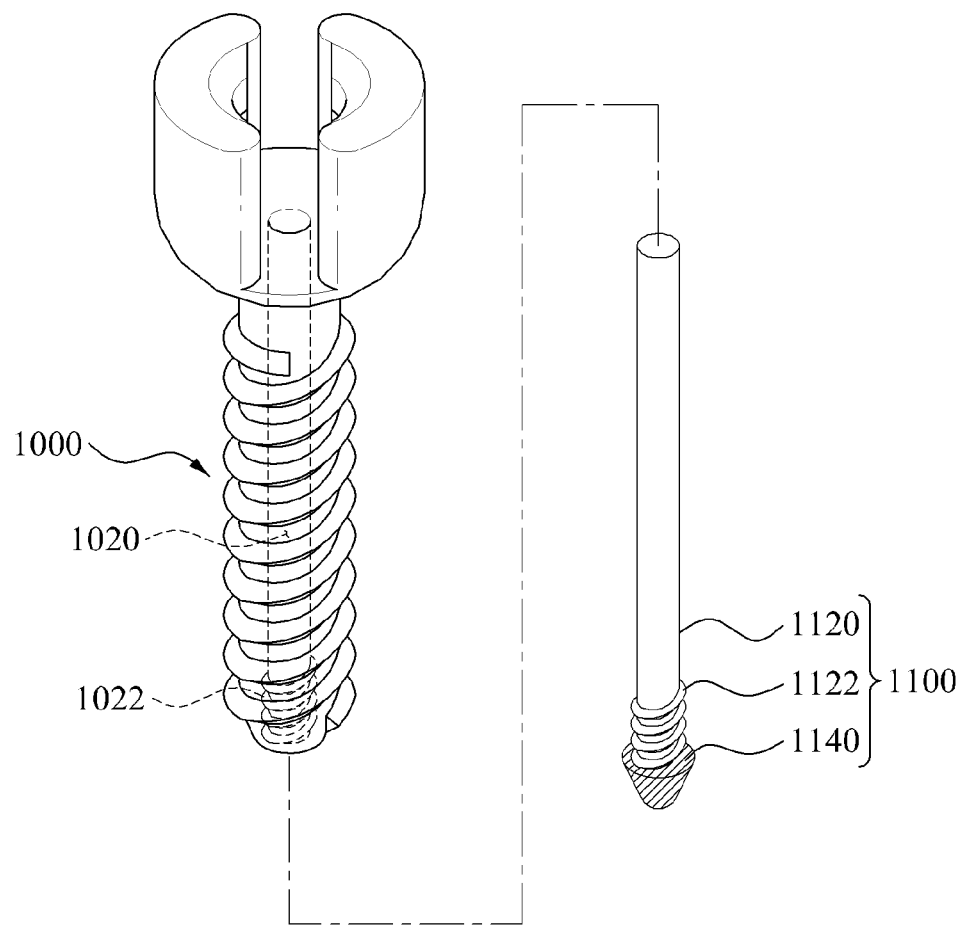
FIG. 8 is a view illustrating an electrode to be connected to a screw body in a medical insertion apparatus according to an embodiment of the present invention.

FIG. 7 is a view illustrating a medical insertion apparatus 20 according to another embodiment of the present invention, and FIG. 8 is a view illustrating an electrode 1100 to be connected to a screw body 1000 in the medical insertion apparatus 20 according to an embodiment of the present invention.

Referring to FIGS. 7 and 8, the medical insertion apparatus 20 includes a screw body 1000 and an electrode 1100.

The screw body 1000 may be inserted into a body. A thread may be provided on an outer side of the screw body 1000.

The screw body 1000 may be inserted into a spine, a tooth, or a muscle. For example, the screw body 1000 may be configured in a synostosis screw to be inserted into an osseous tissue adjacent to a nerve, in particular, a pedicle screw to be inserted into a spine.

Referring to FIG. 8, a through-hole 1020 is provided in a central portion of the screw body 1000.

The through-hole 1020 is provided for an insertion of the electrode 1100. A shape of the through-hole 1020 may correspond to a shape of the electrode 1100 to be disposed in the through-hole 1020.

For example, when the electrode 1100 to be disposed in the through-hole 1020 has a round cross-section, the through-hole 1020 may also have a round cross-section. When the electrode 1100 is provided in a shape of a cylinder, the through-hole 1020 may also be provided in a shape of a cylinder.

The through-hole 1020 extends in a longitudinal direction of the screw body 1000 from one end of the screw body 1000 to a terminal portion of the screw body 1000.

A thread 1022 is provided in the through-hole 1020 at a position adjacent to the terminal portion of the screw body 1000.

The thread 1022 may be provided in the through-hole 1020 for screw fastening with a thread 1122 provided on the electrode 1100, which will be described in detail later.

The electrode 1100 may be inserted into the through-hole 1020.

The electrode 1100 may be inserted into the through-hole 1020 through the terminal portion of the screw body 1000.

The electrode 1100 may be configured as follows.

The electrode 1100 includes a first portion 1120 extending in the longitudinal direction of the screw body 1000, and a second portion 1140 connected to the first portion 1120 and externally exposed at the terminal portion of the screw body 1000.

The first portion 1120 may be disposed in the through-hole 1020 of the screw body 1000, and the second portion 1140 may be externally exposed at the terminal portion of the screw body 1000.

Thus, the first portion 1120 may be provided to have a shape corresponding to a shape of the through-hole 1020, and the second portion 1140 may be provided to be greater than the through-hole 1020.

When the first portion 1120 is inserted into the through-hole 1020 through the terminal portion of the screw body 1000, the second portion 1140 may be maintained to be externally exposed at the terminal portion of the screw body 1000. Thus, the second portion 1140 may not be inserted into the through-hole 1020.

The thread 1122 to engage with the thread 1022 of the through-hole 1020 is provided on the first portion 1120.

The thread 1122 of the first portion 1120 and the thread 1022 of the through-hole 1020 are provided at corresponding positions.

For example, the thread 1122 of the first portion 1120 and the thread 1022 of the through-hole 1020 may be disposed to be adjacent to the terminal portion of the screw body 1000.

The second portion 1140 is externally exposed at the terminal portion of the screw body 1000. Thus, when the screw body 1000 is in contact with, for example, a nerve or muscle, a contact between the electrode 1100 and the nerve or muscle may be detected.

Although not illustrated in the drawings, the medical insertion apparatus 20 may be used by being connected to a nerve stimulating and monitoring apparatus.

The nerve stimulating and monitoring apparatus may include an apparatus for electromyography (EMG), an evoked potential (EP) test, a motor evoked potential (MEP) test, and a somatosensory evoked potential (SSEP) test.

However, the nerve stimulating and monitoring apparatus is not limited thereto. The nerve stimulating and monitoring apparatus may include any apparatus configured to provide an electrical stimulus to a muscle or nerve, and receive or detect a signal generated in the muscle or nerve in response to the electrical stimulus.

The electrode 1100 provided in the medical insertion apparatus 20 may be connected to the nerve stimulating and monitoring apparatus to apply a minute current directly to a nerve.

Thus, when the electrode 1100 of the medical insertion apparatus 20 is inserted and in contact with a nerve during a surgery or treatment, a current may be applied to the nerve and a signal may be generated in the nerve or muscle. When the generated signal is detected by the nerve stimulating and monitoring apparatus, it may be understood that the medical insertion apparatus 20 is in contact with a nerve.

In this example, the current may be transmitted through the first portion 1120 to the second portion 1140, and the second portion 1140 may be in contact with the nerve or muscle.

The electrode 1100 of the medical insertion apparatus 20 may be connected to the screw body 1000 as follows.

A top end of the first portion 1120 of the electrode 1100 may be inserted into the through-hole 1020 through the terminal portion of the screw body 1000.

When the first portion 1120 is inserted into the through-hole 1020 and the second portion 1140 is disposed to protrude at the terminal portion of the screw body 1000, the thread 1022 of the through-hole 1020 and the tread 1122 of the first portion 1120 may be in contact with each other.

Since the second portion 1140 is provided to be greater than the through-hole 1020, the second portion 1140 may not be inserted into the through-hole 1020. Thus, the second portion 1140 may be in contact with the terminal portion of the screw body 1000.

The electrode 1100 may rotate with respect to the screw body 1000 to enable screw fastening between the thread 1022 of the through-hole 1020 and the thread 1122 of the first portion 1120.

When the screw body 1000 and the electrode 1100 are fastened together, one end of the screw body 1000 and one end of the first portion 1120 may be disposed at identical heights.

The aforementioned nerve stimulating and monitoring apparatus may transmit a current from the through-hole 1020 through the exposed end portion of the first portion 1120.

Conversely, the electrode 1100 of the medical insertion apparatus 20 may be separated from the screw body 1000 as follows.

The electrode 1100 may rotate with respect to the screw body 1000 in a direction opposite to a direction in which the electrode 1100 rotates with respect to the screw body 1000 to fasten the screw body 1000 and the electrode 1100 together.

Thus, the screw fastening between the tread 1022 of the through-hole 1020 and the tread 1122 of the first portion 1120 may be released, and the first portion 1120 may be pulled out from the terminal portion of the screw body 1000.

Since the second portion 1140 is provided to be greater than the through-hole 1020, the second portion 1140 may not be inserted into the through-hole 1120, and the first portion 1120 may not be separated from the screw body 1000 through the one end of the screw body 1000.

As described above, the screw body 1000 and the electrode 1100 may be easily connected to or separated from each other.

Thus, for the medical insertion apparatus 20, a melted electrode material may not need to be inserted into the screw body 1000. Thus, the screw body 1000 and the electrode 1100 may be provided using materials having similar melting points. In addition, the medical insertion apparatus 20 may be processed in a form of an assembly, whereby a defect rate may decrease, processing may be easy, and an overall unit cost of production may decrease.

Descriptions of the medical insertion apparatus 20 are provided above. Hereinafter, a medical insertion apparatus 30 according to still another embodiment and a medical insertion apparatus 40 according to yet another embodiment will be described. Descriptions on configurations similar to the configuration of the medical insertion apparatus 20 will be omitted for conciseness.

Figure 9:
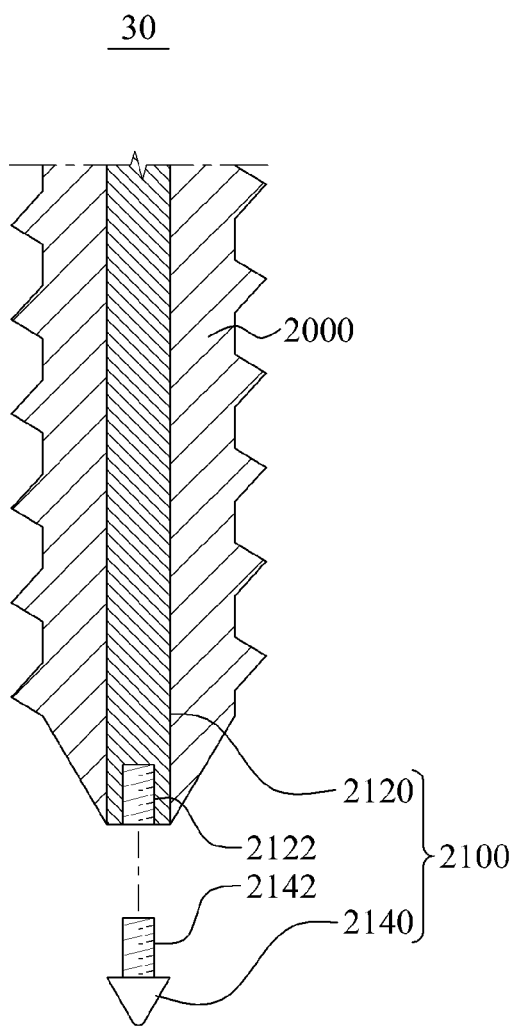
FIG. 9 is a view illustrating a medical insertion apparatus according to still another embodiment of the present invention.

FIG. 9 is a view illustrating the medical insertion apparatus 30 according to still another embodiment of the present invention.

Referring to FIG. 9, the medical insertion apparatus 30 includes a screw body 2000 and an electrode 2100.

The medical insertion apparatus 30 differs from the medical insertion apparatus 20 in that the electrode 2100 is detachably provided.

The electrode 2100 includes a third portion 2120 and a fourth portion 2140.

The electrode 2100 may include platinum, gold, silver, and tungsten, which are biocompatible and excellent in electric conductivity.

The third portion 2120 extends in a longitudinal direction of the screw body 2000 toward one side of the screw body 2000.

A recessed element 2122 is provided at an end portion of the third portion 2120 disposed at a terminal portion of the screw body 2000. The recessed element 2122 may be provided to fasten the third portion 2120 and the fourth portion 2130 together. A thread may be provided on an inner side surface of the recessed element 2122.

The fourth portion 2140 externally protrudes at the terminal portion of the screw body 2000.

FIG. 9 illustrates the fourth portion 2140 being disposed at the terminal portion of the screw body 2000. However, a position of the fourth portion 2140 is not limited thereto. The fourth portion 2140 may be disposed at a position spaced apart from the terminal portion of the screw body 2000.

A protruding element 2142 may be provided at an end portion of the fourth portion 2140 to be connected to the third portion 2120. The protruding element 2142 may be provided to fasten the fourth portion 2140 to the recessed portion 2122 of the third portion 2120. A thread may be provided on an outer side surface of the protruding element 2142.

As described above, the recessed element 2122 provided in the third portion 2120 of the electrode 2000 and the protruding element 2142 provided in the fourth portion 2140 of the electrode 2000 may be provided symmetrically. Through screw fastening therebetween, the third portion 2120 and the fourth portion 2140 may be connected to or separated from each other.

However, it is obvious that the third portion 2120 and the fourth portion 2140 may be connected to each other through interference fit, rather than screw fastening.

The externally exposed portion of the electrode 2000 may be provided in a replaceable structure in the medical insertion apparatus 30. Thus, the electrode 2000 may be easily maintained.

Figure 10:
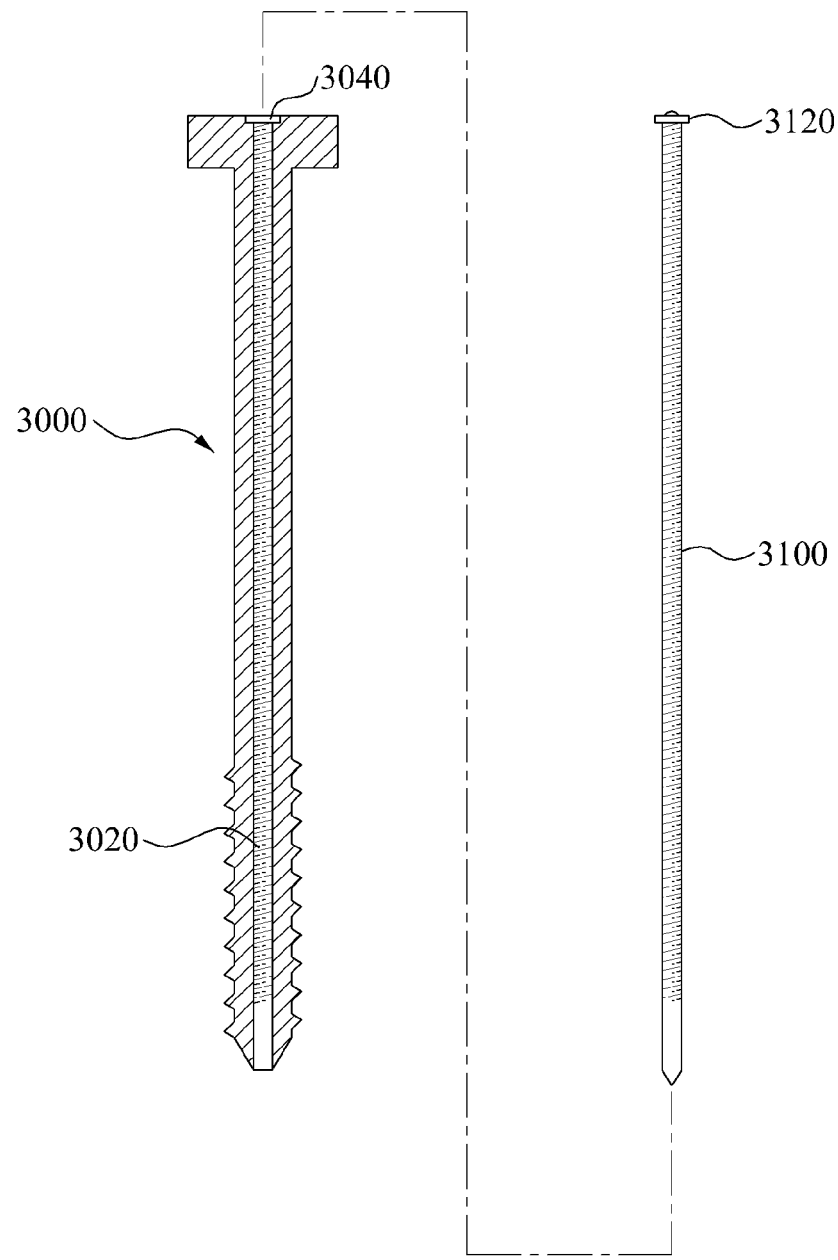
FIG. 10 is a view illustrating a medical insertion apparatus according to yet another embodiment of the present invention.

FIG. 10 is a view illustrating the medical insertion apparatus 40 according to yet another embodiment of the present invention.

Referring to FIG. 10, the medical insertion apparatus 40 includes a screw body 3000 and an electrode 3100.

A through-hole 3020 is provided in an internal portion of the screw body 3000 for an insertion of the electrode 3100.

The through-hole 3020 is provided to extend in a longitudinal direction of the screw body 3000 from one end of the screw body 3000 to a terminal portion of the screw body 3000.

A thread may be provided on an inner side surface of the through-hole 3020. The thread of the through-hole 3020 may be provided for screw fastening with a thread provided on an outer side surface of the electrode 3100. The thread of the through-hole 3000 may be provided to correspond to the thread provided on the outer side surface of the electrode 3100.

The electrode 3100 may be inserted into the through-hole 3020 through the one end of the screw body 3000. The one end of the screw body 3000 refers to an opposite side of the terminal portion of the screw body 3000.

The electrode 3100 may be provided in a shape corresponding to a shape of the through-hole 3020. The electrode 3100 may be externally exposed at the terminal portion of the screw body 3000.

To restrict a separation of the electrode 3100 from the through-hole 3020 after the electrode 3100 is connected to the through-hole 3020 through screw fastening, a guide recess 3040 and a guide protrusion 3120 may be provided symmetrically at the one end of the screw body 3000 and one end of the electrode 3100, respectively.

Although FIG. 10 illustrates the guide recess 3040 being provided at the screw body 3000 and the guide protrusion 3120 being provided at the electrode 3100, it is obvious that the guide protrusion 3120 may also be provided at the screw body 3000 and the guide recess 3040 may also be provided at the electrode 3100.

As described above, for the medical insertion apparatus 40, the screw body 3000 and the electrode 3100 may be provided in a connectable or separable structure. Thus, the electrode 3100 may be easily connected to or separated from the screw body 3000. In addition, the screw body 3000 and the electrode 3100 may be provided using materials having similar melting points.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A medical insertion apparatus comprising:
   a screw body to be inserted into a body, wherein the screw body is a first material; and
   an electrode positioned in the screw body, wherein the electrode is formed to include an externally exposed portion in which the electrode is externally exposed through the screw body, and wherein the electrode is a second material having a greater electrical conductivity than the first material,
   wherein a through-hole is formed in the screw body and the electrode in a first direction, the first direction corresponding to a longitudinal direction of the screw body, the through-hole extending in the first direction from one end of the screw body to a terminal portion of the screw body,
   wherein the externally exposed portion of the electrode is provided in a second direction different from the first direction at a position spaced apart from the terminal portion of the screw body on an outer circumference of the screw body,
   wherein a first portion of the through-hole is formed to extend in a central portion of the screw body and the electrode and a second portion of the through-hole is formed to extend through the central portion of the screw body toward the terminal portion of the screw body without extending through the electrode,
   wherein the externally exposed portion of the electrode is oriented in the second direction and an end of the through-hole is oriented in the first direction,
   wherein the screw body that is the first material and the electrode that is the second material are in direct contact with one another
   wherein the first material is titanium, and
   wherein the second material is selected from the group consisting of platinum, gold, silver and tungsten.

2. The medical insertion apparatus of claim 1, wherein the electrode is formed using a method of filling with a melted electrode material in the screw body and hardening the electrode material by cooling the electrode material at room temperature.

3. The medical insertion apparatus of claim 1, wherein a guide element is disposed in the through-hole to guide an insertion of the screw body into the body.

4. A medical insertion apparatus comprising:
   a screw body to be inserted into a body, wherein the screw body is titanium; and
   an electrode positioned in the screw body, wherein the electrode is formed to include an externally exposed portion in which the electrode is externally exposed through the screw body, and wherein the electrode is a material having a greater electrical conductivity than the screw body,
   wherein a through-hole is formed in the screw body and the electrode in a first direction, the first direction corresponding to a longitudinal direction of the screw body, the through-hole extending in the first direction from one end of the screw body to a terminal portion of the screw body,
   wherein the externally exposed portion of the electrode is provided in a second direction different from the first direction at a position spaced apart from the terminal portion of the screw body on an outer circumference of the screw body, wherein a first portion of the through-hole is formed to extend in a central portion of the screw body and the electrode and a second portion of the through-hole is formed to extend through the central portion of the screw body toward the terminal portion of the screw body without extending through the electrode, wherein the externally exposed portion of the electrode is oriented in the second direction and an end of the through-hole is oriented in the first direction, and wherein the screw body and the electrode that is the material having a greater electrical conductivity than the screw body are in direct contact with one another.

\* \* \* \* \*